United States Patent
Cavia et al.

(10) Patent No.: US 8,506,769 B2
(45) Date of Patent: Aug. 13, 2013

(54) BIOSENSOR SUPPORT

(75) Inventors: Daniel Arquero Cavia, Derio (ES);
Asier Albizu Lluvia, Derio (ES)

(73) Assignee: Biolan Microbiosensores, S.L., Derio (Bizkaia) (ES)

( * ) Notice: Subject to any disclaimer, the term of this patent is extended or adjusted under 35 U.S.C. 154(b) by 173 days.

(21) Appl. No.: 13/003,472

(22) PCT Filed: Jul. 10, 2009

(86) PCT No.: PCT/ES2009/000362
§ 371 (c)(1),
(2), (4) Date: Aug. 3, 2011

(87) PCT Pub. No.: WO2010/004069
PCT Pub. Date: Jan. 14, 2010

(65) Prior Publication Data
US 2012/0090994 A1    Apr. 19, 2012

(30) Foreign Application Priority Data
Jul. 11, 2008  (ES) .................................. 200802126

(51) Int. Cl.
C25B 11/08    (2006.01)
(52) U.S. Cl.
USPC ........................................................ 204/292

(58) Field of Classification Search
USPC ...................... 204/279–292, 297.01
See application file for complete search history.

(56) References Cited

U.S. PATENT DOCUMENTS

| 3,770,607 A | 11/1973 | Williams |
| 4,224,125 A | 9/1980 | Nakamura et al. |
| 4,354,913 A * | 10/1982 | Pungor et al. ............ 204/403.08 |
| 4,440,620 A | 4/1984 | Ono et al. |
| 4,820,399 A | 4/1989 | Senda et al. |

FOREIGN PATENT DOCUMENTS

| EP | 0400918 A | 12/1990 |
| GB | 2054859 A | 2/1981 |

* cited by examiner

*Primary Examiner* — J. Christopher Ball
(74) *Attorney, Agent, or Firm* — Lucas & Mercanti, LLP

(57) ABSTRACT

The invention relates to a biosensor support comprising a cylinder (1) consisting of a non-electroconductive material and having: a through-hole (2) coaxial to the axis of the cylinder (1); a metal rod (3) arranged in said opening (2), with its upper end ($3_1$) level with the top base ($1_1$) of the cylinder (1); a layer/coating of noble metal (4) of between 1 and 1000 nanometers, arranged on the top base ($1_1$) of the cylinder, and a protector (5) consisting of a non-electroconductive material arranged on the layer/coating of noble metal (4) in the area where the layer (4) joins the metal rod (3), said protector covering a surface having a diameter ($Ø_2$) larger than the diameter of the rod (3). The invention is applicable to the specific detection of substances in aqueous media.

5 Claims, 2 Drawing Sheets

BIOSENSOR SUPPORT

The present application is a 371 of International application PCT/ES2009/000362 filed Jul. 10, 2009, which claims priority of ES P-200802126, filed Jul. 11, 2008, the priority of these applications is hereby claimed and these applications are incorporated herein by reference.

This invention is based on a device which serves as a base for the installation of an enzymatic substance or another of any kind with the purpose of creating a biosensor for the specific detection of substances in aqueous medias. Similar supports are already known in the state of the art, but they is are based on solid plates, preferably circular, made of gold, carbon, or platinum. Said plates are manufactured in pure metal with a thickness of one or several millimeters. The outer part, where the enzymes are deposited, is polished and is at the same level as the plastic cylinder that houses it. In the inner part of said plastic cylinder, on the inner face of the metal plate, a resistor built with compressed carbon powder is installed. The typical impedance of this carbon powder is usually less than ten ohms. After this compressed carbon, a brass bar is installed, preferably so that when it comes out on the end opposite the gold plate, through the plastic cylinder that houses it, it can receive the electric signal from the enzyme deposited on the plate.

Also cited as state of the art are Patents GB2054859, U.S. Pat. No. 4,224,125 and U.S. Pat. No. 3,770,607.

Document GB2054859 discloses a biosensor support that consists of:
- a cylinder (3) that is made of material which is non-electroconductive, which has a through-hole that is coaxial to the axis of the cylinder (3)
- a metal rod (4) arranged in said opening (2) with its upper end level with the top base of the cylinder (3)
- a layer/plate/coating of noble metal (4) arranged on said top base
- a protector consisting of a permeable polypropylene film (6) arranged on the layer/plate/coating of noble metal (4).

The plate, preferably of gold has a diameter of between 3 and 6 mm.

This type of support for the construction of biosensors has the disadvantage that the electric signal from the chemical reaction of the enzyme is very low. The tests performed with enzymes, preferably glucanase, for the determination of the gluconic acid, show that for a plate that is 3 mm in diameter and 0.1 mm thick, the response of the enzyme was hardly 5 nanoamperes.

Increasing the diameter of the gold plate to 5 mm, the signal was hardly increased by 2 nanoamperes.

The biosensor, thus constructed, when put into the potentiostatic electronic circuit, displays gauging problems due to the very low electric response signal of the enzyme; moreover, misrepresents the data, as it varies approximately 2 nanoamperes for each centigrade degree. This makes it necessary to rigorously maintain the aqueous media at as constant temperature as is possible.

This invention solves this problem of low enzyme signal response in the presence of the chemical substance for which it has been designed. Likewise, it is valid for any enzymatic substance, as the high response of the is signal is mainly the result of the way in which the support which is the subject matter of this patent is built.

Enzymatic substances need a noble metal or carbon, to be placed to provide a response to the substance for which it was designed. This support, preferably made of gold, cannot be connected directly with a cable or electroconductive rod to the potentiostatic electronic circuit. An impedor must be installed that in commercial sensors, up to now, has been done with compressed carbon. This carbon must be in direct contact with the plate, mainly made of gold, and a conventional electronic resistor cannot be installed. But as the gold plate where the enzyme is deposited is perfectly electroconductive, the electronic signal produced by the enzyme is disguised with respect to the high parasitic or base signal generated by the potentiostatic electronic circuit.

The biosensor support that is the subject matter of the invention is characterized in that it consists of:

a) A cylinder made of non-electroconductive material, that has a through-hole that is coaxial to the axis of the cylinder.

b) A metal rod, arranged in said opening with its upper end level with the top base of the cylinder.

c) a layer/coating of noble metal between 1 and 1000 nanometers, thick, arranged on said top base.

d) a protector consisting of a non-electroconductive material, arranged on the layer/coating of noble metal in the area where the layer joins the metal rod covering a surface with a diameter larger than the diameter of the rod.

This invention solves the problem of the low signal delivered by the enzyme deposited on the biosensor support on the presence of the chemical substance for which it was designed. Moreover, it enormously reduces the parasitic or base line signal generated by the potentiostatic electronic circuit. Due to the topology applied for its manufacturing, the manufacturing price is approximately 300 times less than the one currently in the market. The electric signal delivered by the enzyme is approximately 30 times greater than any current support for biosensors; it can be increased exponentially by increasing its diameter.

This support for biosensors is oriented to a single use. Once the function of the enzyme has finished, it is disposed of.

To better understand the subject matter of this invention, a preferable way of practical embodiment is shown on the diagrams, subject to additional changes that do not alter its essential nature.

Figure 1:
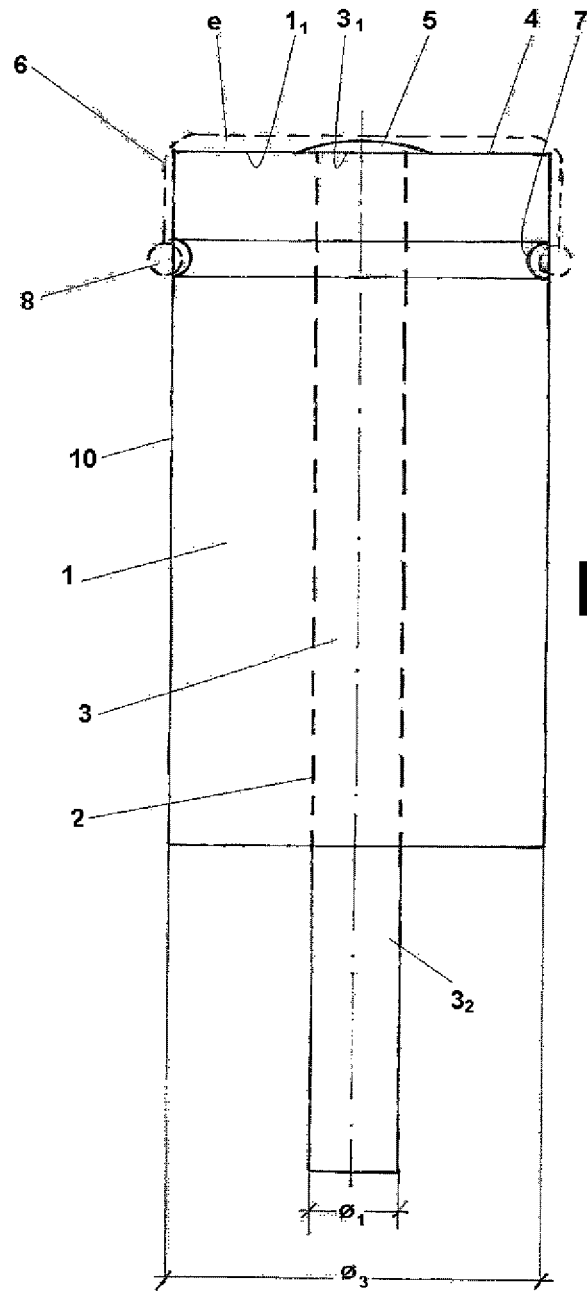
FIG. 1 is a schematic elevation view of the biosensor that is the subject matter of the invention.
Figure 2:
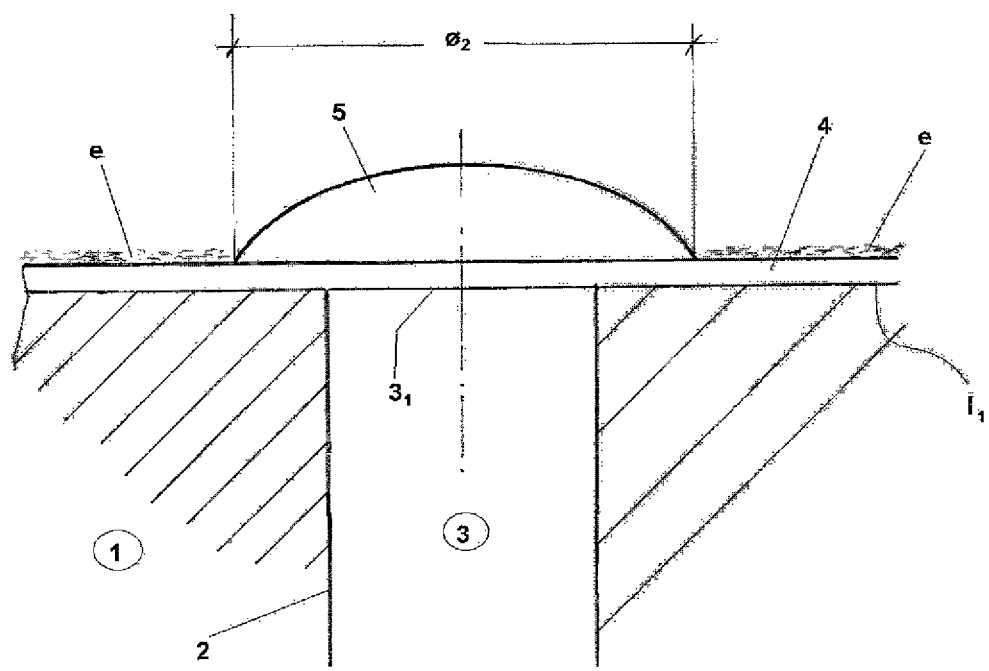
FIG. 2 is a much enlarged section view of the area where the rod (3)/joins the layer of noble metal (4).

Described below is an example of practical, non-limiting embodiment of this invention.

The biosensor support is comprised of a plastic cylinder (1) de, preferably polyvinyl chloride, with a through-hole (2) in its centre, making of it a tube. The diameter of the cylinder (1) can be of any diameter ($\varnothing_3$) but 10 mm. is preferable. In the through-hole (2) a metal rod (3) is inserted, such as stainless steel, copper, brass, etc. (preferably brass) with the single purpose of transporting the flow of electrons generated by the enzymes (e) that will be arranged on the top base ($1_1$) of the plastic cylinder (1) to the potentiostatic electronic circuit (not represented).

Said metal rod (3) must be of a diameter ($\varnothing_1$) that is much smaller than the diameter of the plastic cylinder; preferably 3 mm or less $\varnothing_1 \ll \varnothing_3$.

The upper end ($3_1$) of this brass rod (3) is left level with the plastic to cylinder (1) and at the other end ($3_2$) it is allowed to protrude 5 mm or any other size for its subsequent fastening to the potentiostatic electronic circuit.

The area of the plastic cylinder (1) where the brass rod (3) is left level is face-milled/polished. For this purpose, a machine tool such as a low-speed revolution mill will preferably be used in order to not melt the plastic cylinder with the friction. The surface, polished in this fashion, must be left as smooth as possible, without burning the plastic in the machining due to excess speed of the milling or polishing machine tool.

In turn, on the plastic cylinder (1) on its side surface (10) and at a preferable distance of 2 mm from the top edge of the polished area, a groove is made (7) in thoroidal shape for future fastening of an O-ring seal (8) to fasten a permeable or osmotic membrane (6) such as those used in dialysis.

Once the support of the biosensor is milled and prepared, a layer of gold between 1 and 1000 nanometers thick is applied to it, preferably between 30 and 100 nanometers, depending on the behaviour of other enzymes with regard to the response of generation of the flow of electrons or electric current with respect to the presence of the substance for which it has been designed. This gold bath is applied by sputtering with a commercial unit for this purpose.

With this coating the entire polished area of the plastic cylinder (1) and the brass rod (3) is made electroconductive.

This gold, as it is such a thin layer, measured in nanometers, has impedance to the passage of electric current that is approximately 10 ohms from the edge to its centre.

The problematic gold plated area is the centre of the plastic cylinder (1), precisely the area where the brass rod (3) is housed. If the enzyme (e) deposited on the gold touches this area, it will produce an undesired residual is base or parasitic signal of about 50 or 100 times the signal that the enzyme (e) would produce on the presence of the substance for which it was designed, resulting in very anomalous operation. The electric signal produced by the enzyme would be disguised by this parasitic signal.

To prevent the exposure of the enzyme (e) to the central area where the brass rod (3) is located under the gold coating (4), a protector, glue or preferably a small drop (5) of epoxy resin is deposited; this can be any other non-conductive substance adhering to the material of the cylinder, or even a cap designed for this purpose. Thus, the enzyme will only be deposited in the entire polished crown of the plastic cylinder (1) that is gold-plated (4) except in its central area covered preferably by a drop (5) of epoxy resin.

The drop or protector (5) will preferably be of a material that adheres to gold.

The enzyme (e) deposited on this support which is the subject matter of patent is covered with a permeable or osmotic (6) membrane such as those used in dialysis, and is fastened to the side of the plastic cylinder (1) by to an O-ring seal (8) which, in turn, fits into the side recess (7) in thoroidal shape which is made in the plastic cylinder (1) formed by the biosensor support. The permeable membrane (6) must be perfectly tightened against the polished face ($1_1$) of the plastic cylinder (1) in order to immobilize the enzyme (e) and force it to preferably stay as near as possible to the gold plated area.

Without means of fastening/tightening of the membrane (6) such as this recess for the installation of the O-ring seal (8), the permeable membrane (6) could move and cause the biosensor designed in such a fashion to not function correctly, due to not forcing the enzyme (e) to remain nearest the gold plated area.

The permeable membrane (6) could also be substituted with a permeable liquid membrane.

The invention claimed is:

1. Biosensor support, comprising:
   a) a cylinder of non-electroconductive material, having a through-hole coaxial to the axis of the cylinder
   b) a metal rod arranged in said through-hole with an upper end level with the top base of the cylinder
   c) a layer of noble metal, of between 1 and 1000 nanometers, arranged on said top base; and
   d) a protector of a non-electroconductive material arranged on the layer of noble metal in an area where said layer joins the metal rod and covering a surface with a diameter larger than the diameter of the rod so that an enzyme is deposited on the layer of noble metal except in a central area covered by the protector.

2. Biosensor support, according to claim 1, wherein the cylinder of non-conductive material has means on its side for fastening of a membrane.

3. Biosensor support, according to claim 1, wherein the layer is made of gold with a thickness of between 30 and 100 nanometers.

4. Biosensor support, according to claim 2, wherein the membrane can be a permeable membrane or a liquid permeable membrane.

5. Biosensor support, according to claim 1, wherein the protector is a drop of a resin that adheres to the layer of noble metal.

* * * * *

UNITED STATES PATENT AND TRADEMARK OFFICE
CERTIFICATE OF CORRECTION

PATENT NO.      : 8,506,769 B2                                          Page 1 of 1
APPLICATION NO. : 13/003472
DATED           : August 13, 2013
INVENTOR(S)     : Cavia et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 379 days.

Signed and Sealed this

Fifteenth Day of September, 2015

Michelle K. Lee
*Director of the United States Patent and Trademark Office*